(12) United States Patent
Bergman et al.

(10) Patent No.: US 8,273,926 B2
(45) Date of Patent: Sep. 25, 2012

(54) METHOD OF CONVERTING A POLYOL TO AN OLEFIN

(75) Inventors: Robert G. Bergman, Kensington, CA (US); Jonathan A. Ellman, Oakland, CA (US); Elena Arceo Rebollo, Oakland, CA (US); Peter C. Marsden, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 486 days.

(21) Appl. No.: 12/509,985

(22) Filed: Jul. 27, 2009

(65) Prior Publication Data
US 2009/0287004 A1 Nov. 19, 2009

Related U.S. Application Data

(63) Continuation-in-part of application No. PCT/US2008/052111, filed on Jan. 25, 2008.

(60) Provisional application No. 60/886,661, filed on Jan. 26, 2007.

(51) Int. Cl.
*C07C 1/00* (2006.01)
*C07C 33/03* (2006.01)

(52) U.S. Cl. ............... 568/909.5; 585/638; 585/639

(58) Field of Classification Search ............ 568/852, 568/909.5; 585/639, 638
See application file for complete search history.

(56) References Cited

U.S. PATENT DOCUMENTS

| 901,298 A | 12/1907 | Von Kapff |
| 5,789,236 A | 8/1998 | Jenneman |
| 6,878,696 B2 | 4/2005 | Schmid et al. |

FOREIGN PATENT DOCUMENTS

| DE | 199873 | 1/1907 |
| DE | 520939 | 4/1931 |

OTHER PUBLICATIONS

Kamm et al, Organic Syntheses, Coll. vol. 1, p. 42(1941); vol. 1, p. 15(1921), 3 pages.*
Grant et al, Grant & Hackh's Chemical Dictionary, fifth ed. 1987, McGraw-Hill Book Co. p. 265, 3 pages.*
Buijs, W., (1999). "The Mechanism of Phenol Formation in the Down Phenol Pricess," Journal of Molecular Catalysis: Chemical 146:237-246.
Gibson, J.M. et al., (2001), "Benzene-Free Synthesis if Phenol," Angewandte Chemie International Edition 40 (10):1945-1948.
International Search Report and International Written Opinion mailed May 29, 2008, for PCT/US2008/052111 filed on Jan. 28, 2008, 7 pages.
Ran, N. et al., (2011), "Benzene-Free Synthesis of Hydroquinone," Journal of the American Chemical Society, 123:10927-10934.

* cited by examiner

*Primary Examiner* — Taylor Victor Oh
(74) *Attorney, Agent, or Firm* — Robin C. Chiang; Michelle Chew Wong; Lawrence Berkeley

(57) ABSTRACT

A method of preparing an olefin comprising: reacting a polyol in the presence of a carboxylic acid, such that an olefin is produced by the deoxygenation of the polyol. The reacting step can comprise (a) providing a composition comprising the polyol, (b) heating the composition, and (c) introducing the carboxylic acid to the composition wherein the introducing step occurs prior to, at the same time as, or subsequent to the heating step. In one embodiment, the polyol is glycerol, the carboxylic acid is formic acid, and the olefin is allyl alcohol, which is produced at a yield of about 80% or greater.

32 Claims, 3 Drawing Sheets

1,2-octanediol 1,2-decanediol cis-1,2-cyclooctanediol 1,2,3-cyclohexanetriol 1,2,3-hexanetriol 1,2,3-butanetriol meso-Erythritol Xylitol Mannitol Sorbitol Arabitol Conduritols (1,2,3,4-cyclohexenetetrol)

*myo*-Inositol    Maltitol    Isomalt

Lactitol    Sucrose (saccharose)

Maltose    Lactose

US 8,273,926 B2

METHOD OF CONVERTING A POLYOL TO AN OLEFIN

CROSS-REFERENCE TO RELATED APPLICATIONS

This application claims priority as a continuation-in-part application from PCT International Patent Application No. PCT/US08/52111, filed Jan. 25, 2008, which claims priority to U.S. Provisional Patent Application Ser. No. 60/886,661, filed on Jan. 26, 2007; both of which are hereby incorporated by reference in their entireties.

STATEMENT OF GOVERNMENTAL SUPPORT

This invention was made with government support under Contract No. DE-AC02-05CH11231 awarded by the U.S. Department of Energy. The government has certain rights in the invention.

BACKGROUND OF THE INVENTION

1. Field of the Invention

The present invention relates to uses of biodiesel production byproducts and other materials related to biomass, including the conversion of glycerol from biodiesel production to allyl alcohol, for use as in the synthesis of polymers and carbon-based products.

2. Related Art

As biomass is the only sustainable carbon resource and fossil resources are predicted to be exhausted in a few decades, biomass refinery processes must be developed to replace petroleum feedstocks. This has directed many researchers' interests to the use of biomass as a source of energy and chemical intermediates. The processing technology for fossil raw materials is well known and developed, but it differs radically from bio-feedstocks chemical transformations. A combined effort of companies and academic laboratories is needed to make biomass competitive with fossil raw materials.

Biodiesel produced from soybean oil generates large amounts of glycerol as a byproduct which is currently in oversupply. There is currently strong interest in developing ways to produce industrially important chemicals from renewable biological sources rather than petroleum, such as allyl alcohol. Allyl alcohol is currently made from propylene, which is a petroleum feedstock. Allyl alcohol is often used as a starting material in making various polymers, pharmaceuticals, pesticides and other allyl-substituted compounds Biomass-derived raw materials contain excess functionality, usually having a high oxygen content, which makes them problematical for use as fuels and petrochemicals. The challenge in this field, therefore, is to develop methods to control the functionality in the final products, especially to remove oxygen and replace it with hydrogen and/or carbon-carbon multiple bonds. Reasonable targets for such processes involve dehydration or deoxygenation, which can lead to the formation of olefins or cyclic anhydride derivatives.

Currently there is no industrial process for the large-scale preparation of allyl alcohol from glycerol. As described below, the most effective synthesis in the open literature, which was published many years ago, is not very adequate. This procedure, described in Organic Syntheses, Coll. Vol. 1, p. 42 (1941); Vol. 1, p. 15 (1921), requires heating of glycerol and acid to produce allyl alcohol. However, as it notes, "slow heating causes charring and formation of much acrolein, and thus gives a very low yield of allyl alcohol." Furthermore, more rapid heating is somewhat irreproducible and does not give yields above 50%. Thus, it would be beneficial to provide a method for carrying out this synthesis that is more reliable and that provides a pure product of allyl alcohol in sufficient yield quantities.

BRIEF SUMMARY OF THE INVENTION

The present invention provides a method of preparing an olefin comprising: reacting a polyol in the presence of a carboxylic acid such that an olefin is produced. The reacting step can comprise (a) providing a composition comprising the polyol, (b) heating the composition, and (c) introducing the carboxylic acid to the composition wherein the introducing step occurs prior to, at the same time as, or subsequent to the heating step. Optionally, the composition can further comprise a solvent. Optionally the composition is exposed to an inert atmosphere at any time during the reacting step, such as the heating step. The olefin is produced by the deoxygenation of the polyol.

The present invention provides for a process for the preparation of an olefin, cyclic or acyclic, functionalized or not with a hydroxy, aldehyde or ester group, from a polyol, including but not limited to, diols, triols, sugar polyols, monoanhydro sugar polyols, sugars, or their formic acid esters thereof. The process comprises heating the polyol in the presence of a suitable carboxylic acid, such as formic acid, and optionally under an inert atmosphere. The inert atmosphere can be an inert gas such as argon or nitrogen. Optionally the selected starting materials might be combined with a solvent, such as tetraglyme, water, sulfolane, or the like. The resulting products can be obtained in very high purity and in sufficient yield. FIG. 1 shows several examples of the deoxygenation reaction. The polyol is deoxygenated to produce the olefin.

The present invention also provides a method of synthesis of allyl alcohol from glycerol, whereby allyl alcohol is produced at a yield of 80% or greater, comprising the steps of: providing glycerol and a carboxylic acid, to a reaction mixture, heating the reaction mixture under an inert atmosphere, distilling allyl alcohol from the reaction mixture.

The present invention also provides a process for synthesis of allyl alcohol from glycerol, comprising the steps of: (a) providing glycerol and formic acid to a reaction mixture, (b) heating the reaction mixture under an inert atmosphere to between about 230° C. to about 240° C., and (c) distilling allyl alcohol from the reaction mixture, whereby allyl alcohol is produced at a yield of about 80% or greater.

In one embodiment, the inert atmosphere is an inert gas, such as nitrogen and argon. In another embodiment, in the heating step (b), the reaction mixture is heated to about 235° C. In another embodiment, during the distillation step (c), the reaction mixture is heated to between about 230° C. and about 240° C.

The present invention also provides for an apparatus set up to carry out the method of the present invention. The apparatus can comprise a vessel comprising the composition, a means of heating the vessel, and optionally a condenser set or distillation set in communication with the vessel. The apparatus can further comprise a means to bubble an inert atmosphere through the composition. The condenser set can comprise a fractioning column and a reflux condenser. The distillation set can comprise a fractioning column in communication with a reflux condenser and a collecting vessel.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
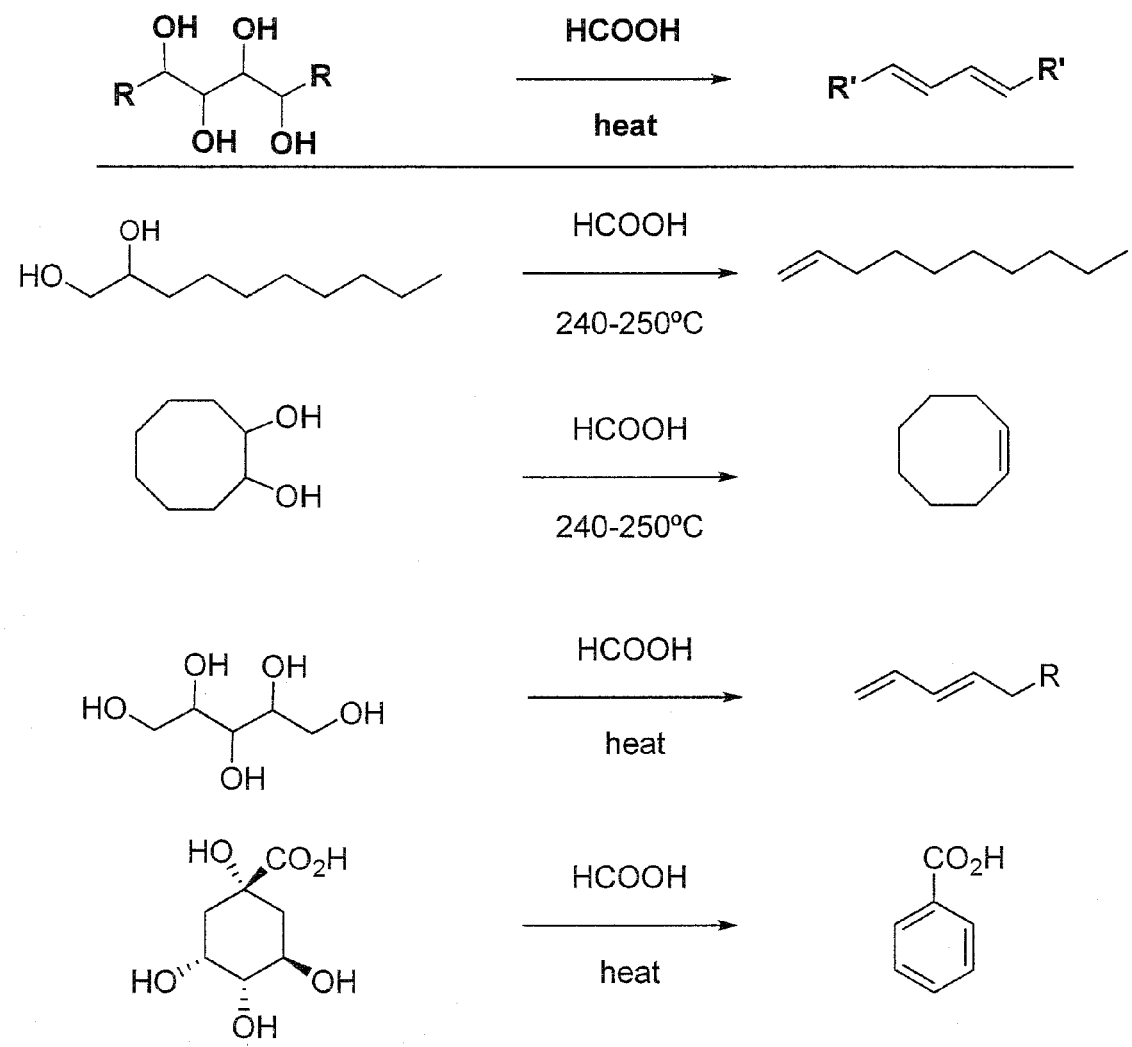
FIG. 1 shows examples of reactions carried out by the present invention.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a polyol" includes a plurality of such polyols, and so forth.

These and other objects, advantages, and features of the invention will become apparent to those persons skilled in the art upon reading the details of the invention as more fully described below.

Definitions

As used herein, by the term "olefin", it is meant an unsaturated chemical compound containing at least one carbon-to-carbon double bond.

As used herein, by the term, "glycerol", it is meant the chemical product, $HOCH_2(CHOH)CH_2OH$, which is also commonly referred to as trihydroxypropane or glycerin.

As used herein, by the term, "about," it is meant to include ±5 of the value(s) indicated.

As used herein, by the term "diol" refers to a chemical compound containing two hydroxyl groups.

As used herein, by the term "triol" refers to a chemical compound containing three hydroxyl groups.

As used herein, by the term "polyol" refers to a polyhydric alcohol, or polyalcohol, that is, an alcohol containing a plurality of hydroxyl groups.

As used herein, by the term "sugar polyol", also known as alditols, refers to a hydrogenated form of carbohydrate whose carbonyl group (aldehyde or ketone) has been reduced to a primary or secondary hydroxyl group.

Descriptions of the Embodiments

The present invention provides a method of preparing an olefin comprising: reacting a polyol in the presence of a carboxylic acid such that an olefin is produced. The reacting step can comprise (a) providing a composition comprising the polyol, (b) heating the composition, and (c) introducing the carboxylic acid to the composition wherein the introducing step occurs prior to, at the same time as, or subsequent to the heating step. Optionally, the composition can further comprise a solvent. Optionally the composition is exposed to an inert atmosphere at any time during the reacting step, such as the heating step. The olefin is produced by the deoxygenation of the polyol.

The present invention provides for a process for the preparation of an olefin, cyclic or acyclic, functionalized or not with a hydroxy, aldehyde, carboxylic acid, or ester group, from a polyol, including but not limited to, diols, triols, sugar polyols, monoanhydro sugar polyols, sugars, or their formic acid esters thereof. The process comprises heating the polyol in the presence of a suitable carboxylic acid, such as formic acid, and optionally under an inert atmosphere. The inert atmosphere can be an inert gas such as argon or nitrogen. Optionally the selected starting materials might be combined with a solvent, such as tetraglyme, water, sulfolane or the like. The resulting products can be obtained in very high purity and in sufficient yield. FIG. 1 shows several examples of the deoxygenation reaction. The deoxygenation of a diol to produce an olefin is a useful synthetic transformation by itself and it is an important process for the modification of natural products in synthesis. This mild, one-step and inexpensive procedure is a useful tool for organic synthesis.

The olefin can be cyclic or acyclic. In some embodiments of the invention, the olefin is an olefin functionalized with a hydroxy group, aldehyde group, carboxylic acid, ester group, or the like. In some embodiments of the invention, the olefin is not functionalized with a hydroxy group, aldehyde group, carboxylic acid, ester group, or the like.

Figure 2:
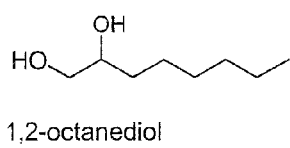
FIG. 2 shows polyols suitable for use in the present invention.
Figure 2:
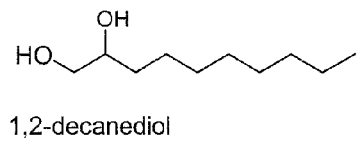
Figure 2:
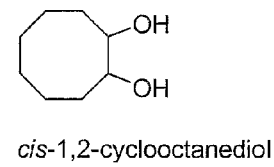
Figure 2:
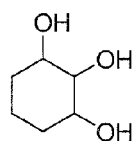
Figure 2:
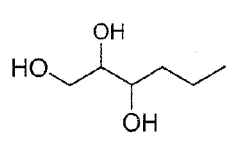
Figure 2:
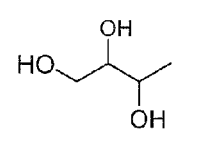
Figure 2:
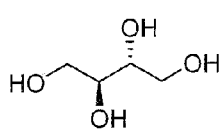
Figure 2:
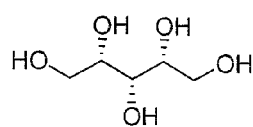
Figure 2:
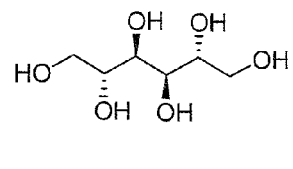
Figure 2:
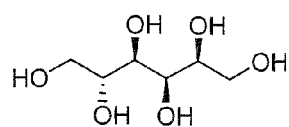
Figure 2:
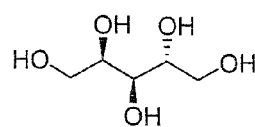
Figure 3:
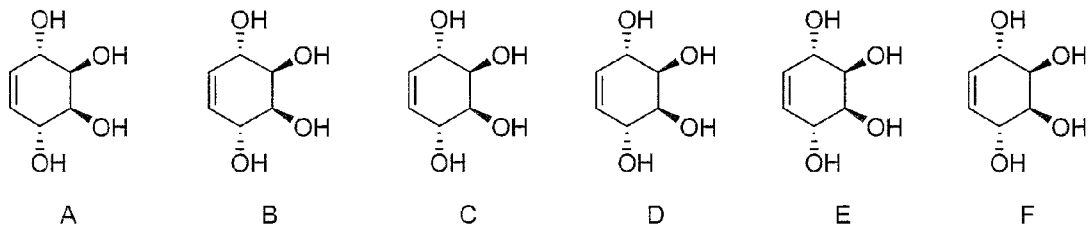
FIG. 3 shows polyols suitable for use in the present invention.
Figure 3:
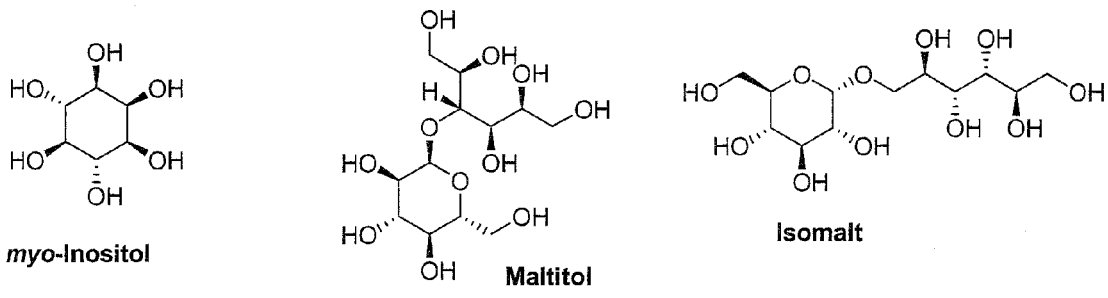
Figure 3:
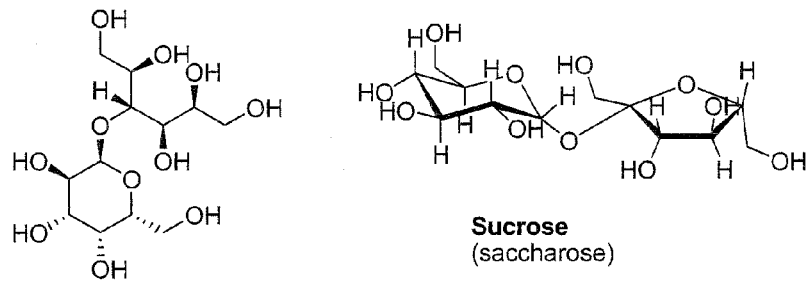
Figure 3:
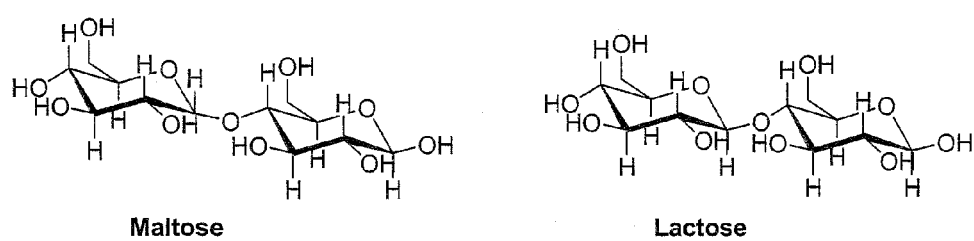

The polyol can be cyclic or acyclic. In some embodiments of the invention, the polyol is a diol or triol. In some embodiments of the invention, the diol is 1,2-hexanediol, 1,2-octanediol, 1,2-decanediol, 1,2-dodecanediol, 1,2-tetradecanediol, 1,2-cyclooctanediol, 1,2-cyclohexanediol, 1,2-cyclopentanediol, or the like, or a mixture thereof. In some embodiments of the invention, the triol is glycerol, 1,4-anhydroerythritol, 1,2,6-trihydroxyhexane, 1,2,3-butanetriol, 1,2,3-hexanetriol, 1,2,3-cyclohexanetriol, or the like, or a mixture thereof. In some embodiments of the invention, the polyol is a sugar polyol, monoanhydro sugar polyol, sugar, or the like, or a formic acid ester thereof, or a mixture thereof. In some embodiments of the invention, the polyol is xylitol, sorbitol, arabinitol, ribitol, mannitol, galactitol, iditol, erythritol, threitol, isomalt, lactitol, quinic acid, shikimic acid, or the like, or a mixture thereof. In some embodiments of the invention, the sugar is glucose, fructose, sucrose, lactose, maltose, or the like, or a mixture thereof. Some of the suitable polyols are shown in FIG. 2 or 3. The polyol can be obtained from biomass-derived carbohydrates, and can have the potential to produce sustainable substitutes for fossil fuels and petroleum-based building blocks used in the production of fine chemicals and plastics.

In some embodiments of the invention, the carboxylic acid is formic acid.

In some embodiments of the invention, the inert atmosphere comprises an inert gas such as argon, nitrogen, or the like, or a mixture thereof.

In some embodiments of the invention, the solvent is tetraglyme, water, sulfolane, or the like, or a mixture thereof.

In some embodiments of the invention, the providing step comprises providing the composition in a vessel, wherein the vessel comprises a material that substantially or essentially does not react with the ingredients in the composition or the olefin, and is substantially or essentially not chemically altered by the heating. Suitable vessels are well known to those skilled in the art.

The polyol is deoxygenated to produce the olefin. The heating step comprises the use of any suitable means of heating, which are well known to those skilled in the art. In some embodiments of the invention, the heating step comprises heating the composition to a temperature from 100° C. to 300° C. In some embodiments of the invention, the heating step comprises heating the composition to a temperature from 200° C. to 300° C. In some embodiments of the invention, the heating step comprises heating the composition to a temperature from 220° C. to 250° C. The heating step can be performed for a time period sufficient for at least 50%, 80%, 90%, or essentially 100% of the polyol to be converted into the olefin, i.e., the yield can be at least 50%, 80%, 90%, or essentially 100%. In some embodiments of the invention, the heating step comprises heating the composition until it is molten. In some embodiments of the invention, the heating step comprises bubbling an inert gas or mixture of inert gases through the composition. The vessel can be in communication with a condenser or distillation apparatus. The condenser apparatus can comprise a fractioning column and a reflux condenser. The distillation apparatus can comprise a reflux condenser and a collecting vessel, such as a flask.

The deoxygenation reaction can be performed at temperatures ranging from about 100° C. to about 300° C. for a length of time sufficient to provide the olefin product. Nitrogen may be bubbled through the mixture during this process, using a perforated tube immersed in the solution. This process may be carried out in a vessel connected to a condenser set or to a distillation set. By the term condenser set it is meant a fractioning column and a reflux condenser. By the term distillation set it is meant a fractioning column connected to a reflux condenser and a collecting flask.

In some embodiments of the invention, the method can further comprise: separating the olefin from the rest of the composition. The separating step can comprise isolating or purifying the olefin.

In some embodiments of the invention, the method can further comprise: neutralizing the olefin, and optionally removing the water produced by the deoxygenation reaction. The neutralizing step can comprise: introducing a suitable carbonate, such as potassium carbonate or sodium carbonate. Following the deoxygenation reaction and distillation, the product may be neutralized and the water removed. For example, neutralization may be accomplished by addition of potassium carbonate or sodium carbonate. For example, water may be removed by decantation or by vacuum evaporation. The desired product may be purified following the deoxygenation procedure. For example, distillation with or without vacuum is used for purification. The parameters for distillation, such as temperature and pressure, will vary depending on the material to be purified.

In some embodiments of the invention, two or more different olefin products may be obtained from the deoxygenation reaction. For example, when erythritol is submitted to the process involving heating in the presence of formic acid, 2,5-dihydrofuran or 1,3-butadiene or a mixture of 2,5-dihydrofuran and 1,3-butadiene is obtained. Variation in the reaction conditions, for example the quantity of formic acid added, a combination of the starting material with formic acid at a temperature lower than the temperature needed for deoxygenation for a certain period of time, the temperature of the deoxygenation process etc can modify the product ratio of 2,5-dihydrofuran and 1,3-butadiene.

The present invention also provides a method of synthesis of allyl alcohol from glycerol, whereby allyl alcohol is produced at a yield of 80% or greater, comprising the steps of: providing glycerol and a carboxylic acid, to a reaction mixture, heating the reaction mixture under an inert atmosphere, distilling allyl alcohol from the reaction mixture.

The present invention also provides a process for synthesis of allyl alcohol from glycerol, comprising the steps of: (a) providing glycerol and formic acid to a reaction mixture, (b) heating the reaction mixture under an inert atmosphere to between about 230° C. to about 240° C., and (c) distilling allyl alcohol from the reaction mixture, whereby allyl alcohol is produced at a yield of about 80% or greater.

In one embodiment, the inert atmosphere is an inert gas, such as nitrogen and argon. In another embodiment, in the heating step (b), the reaction mixture is heated to about 235° C. In another embodiment, during the distillation step (c), the reaction mixture is heated to between about 230° C. and about 240° C.

The present invention provides a method to carry out the synthesis of allyl alcohol from glycerol, producing a clean product in good yield. Glycerol is transformed to allyl alcohol by heating glycerol in a carboxylic acid, the reaction being:

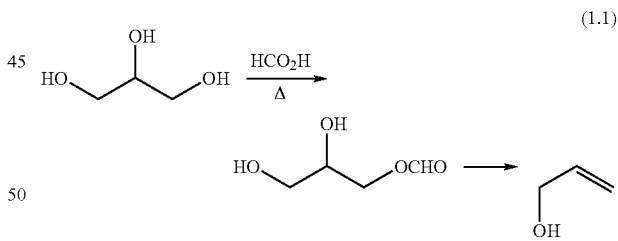

(1.1)

In a particular embodiment, the carboxylic acid used is formic acid, which generates $CO_2$ as a byproduct of allyl alcohol formation.

It was considered that the charring and inadequate yield may be due to the presence of oxygen during the synthesis, resulting in oxidative decomposition of glycerol. Therefore a method was developed to carry out the reaction under an inert atmosphere, in the absence of oxygen. In a particular embodiment, the method is carried out in the presence of an inert gas such as argon or nitrogen. In one embodiment, the synthesis was carried out under nitrogen which eliminated the need for rapid heating, eliminated charring and provided a high yield, 80%, of very pure product. The reaction carried out was:

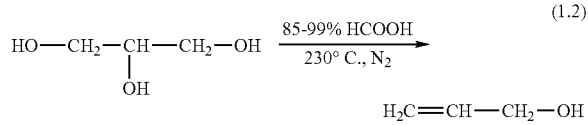

(1.2)

The temperature is raised gradually, until a temperature of between about 230° C. to about 260° C. is reached, such as between about 230° C. to about 240° C., such as about 230° C. to about 235° C. One skilled in the art can determine suitable rates of heating to carry out the reaction. In one embodiment, the temperature of the reaction mixture is raised gradually at rates similar to those used in Example 1. Allyl alcohol is distilled directly from the reaction mixture which results in allyl alcohol with some formic acid and traces of allyl formate and glycerol. Heating is continued during distillation to maintain the temperature between about 230° C. to about 260° C., such as between about 230° C. to about 240° C., and then the mixture is allowed to cool to room temperature.

In a particular embodiment, the total yield is equal to or greater than about 80%. Glycerol, as the starting material, can be put back through the reaction, or may be converted completely to product by further treatment of the product mixture with additional amounts of formic acid. The allyl formate can be hydrolyzed directly to the desired product allyl alcohol with inexpensive sodium hydroxide solution.

The method of the present invention does not require the presence of an activated group, such as cyclic phosphatamides, cyclic sulfates, cyclic thiocarbonates, bis-O,O'-dithioxocarbamates, iodothiocarbonates, orthoesters, cyclic 1-(dimethylamino)methylene acetals or dimesylates. The method of the present invention does not require the presence of a tungsten (IV) salt, titanium reagent, or chlorodiphenyl phosphine/imidazol/iodine.

The method of the present invention does not require the presence of a catalyst such as an inorganic acid (such as phosphoric or sulfuric acid), Lewis acid (such as $ZnCl_2$ and $BF_3$), salt (such as aluminum salts, Th or Zr ions), oxalic acid, zirconium phosphate, Al, Ti, Ca, or In ions, $ZrOCl_2$, V, Zr, Cr, Ti, or porphyrins.

The method of the present invention does not require the presence of p-toluenesulfonic acid, a strong mineral acid, such as sulfuric acid, hydrochloric acid, hydrogen fluoride, a pyridinium salt, an ion exchange resin, or a zeolite.

In one embodiment of the invention, the synthesis of 2,4-pentadien-1-ol from a simple polyol, which can be performed by the method of the present invention. Using the method of the present invention, the preparation of 2,4-pentadien-1-ol does not require starting materials such as 1,4-pentadiene, 2,4-pentadienoic acid, or propargyl alcohol.

This invention also provides a one-step and inexpensive procedure for the deoxygenation of simple vicinal diols that allows the preparation of the corresponding alkene in almost quantitative yield with complete selectivity, and with essentially perfect atom economy, since it requires only heat and no added reagents and results in the formation of minimal waste products. It is therefore more effective and direct than existing methods.

With regard to synthetic reactions involving sugars and polyols, they are biomass derived substances obtained from natural products. Therefore, these compounds are classified as regenerable resources. Presently, there are many industries interested in the transformation of this type of resources into less highly oxygenated materials.

This invention provides an access to intermediates with high industrial potential that could be easily performed on an industrial scale. The use of olefins in industry is extensive. Biomass derived olefins could replace other petrochemical-based monomers in polymer and oligomer production and they could be used in the manufacture of resins as well as in the preparation of diesel fuels, biofuels, or pharmaceuticals.

In one embodiment of the present invention, erythritol is transformed into 2,5-dihydrofuran and/or 1,3-butadiene. 2,5-dihydrofurans are important building blocks for the pharmaceutical and commodity chemical industry, and 1,3-butadiene is extensively used in the industrial production of polymers.

EXAMPLE 1

Preparation of Allyl Alcohol

In a 100 mL three neck round-bottomed flask are placed 150 mmol (13.8 g) of glycerol and 89 mmol of 85 to 99 percent formic acid. The flask is connected with a condenser set: fractioning column, reflux condenser and collecting flask. The temperature in the reaction mixture is monitored by a thermometer. A tube is run from the side arm of the distilling flask to a bubbler containing sodium hydroxide solution. For example, sodium hydroxide dissolved in water for a final concentration of 0.1 M, however, other concentrations of sodium hydroxide can be used.

Nitrogen was bubbled through the mixture, using a perforated tube immersed in the solution, for 20 minutes at room temperature. The mixture was then heated over a preheated sand bath, with continuation of the nitrogen bubbling. The temperature was raised gradually, until a temperature of 235° C. was reached after 30 minutes. Under these conditions, distillation of the product takes place over about 45 minutes. Heating was continued until the temperature reached 230° C. to 260° C. and then the mixture is allowed to cool to room temperature. A second portion of 85 percent formic acid (63.5 mmol) was added and the distillation was repeated in exactly the same manner as described above. Finally a third formic acid/distillation cycle was carried out. The three distillates contain allyl alcohol with some formic acid and traces of allyl formate and glycerol. The total yield was greater than 80%.

EXAMPLE 2

Large-Scale Process of Allyl Alcohol Synthesis

The reaction 1.1 can be carried out as a large-scale process. Calculated amounts of glycerol and a carboxylic acid such as formic acid to form a reaction mixture can be provided to stainless steel vessels for distillation. In a particular embodiment, one may use heating coils surrounding the vessels to enable distillation of allyl alcohol. The temperature in the reaction mixture is monitored. The vessel containing the reaction mixture is also connected to a bubbler containing sodium hydroxide solution. For example, sodium hydroxide dissolved in water can be used.

Nitrogen is bubbled through the mixture, for example, by using a perforated tube immersed in the solution, for a sufficient time at room temperature. The reaction mixture is then heated with continuation of the nitrogen bubbling. The temperature is raised gradually, until a temperature of between about 230 and about 240° C., such as about 235° C., is reached. Under these conditions, distillation of the product takes place. Heating is continued to maintain the temperature between about 230° C. to about 240° C. and then the mixture is allowed to cool to room temperature. Formic acid can be added multiple times and the distillation process repeated in the same manner as described above. The distillates should contain allyl alcohol with some formic acid and traces of allyl formate and glycerol at a high yield. In one embodiment, the total yield is greater than about 80%.

EXAMPLE 3

Large-Scale Process of 1-Octene Synthesis

In a 50 mL three neck round-bottomed flask are placed 20 mmol (2.92 g) of 1,2-octanediol. The flask is fitted with a distillation set: fractioning column, reflux condenser and collecting flask. The temperature is monitored by a thermometer immersed in the reaction mixture. A tube is run from the side arm of the distilling flask to a bubbler containing sodium hydroxide solution. An example would be sodium hydroxide dissolved in water for a final concentration of 0.1 M; however, other concentrations of sodium hydroxide can be used.

The flask is heated at about 60° C. until the starting material is melted, and then 12 mmol of 95 percent formic acid (95%, aqueous) is added. Nitrogen is bubbled through the mixture, using a perforated tube immersed in the solution, for 20 minutes at that temperature. The mixture is then heated over a preheated sand bath, with continuation of the nitrogen bubbling. The temperature rises gradually until a temperature of 235° C. is reached. Under these conditions distillation of the product takes place over about 2 h. Heating is continued until no more distillate appears. A second portion of formic acid (8 mmol) is added and the distillation is repeated in exactly the same manner as described above. Finally a third formic acid/distillation cycle is carried out. The distillate contains 1-decene with some formic acid and water. Sodium carbonate is added to the distillate to neutralize the formic acid and water is removed by decantation. The resulting product is pure 1-octene and the total yield is greater than 90%.

EXAMPLE 4

Synthesis of Benzoic Acid Via Acid-Mediated Deoxygenation of the Glucose Derivatives Quinic Acid and Shikimic Acid Modern society depends on fossil resources to produce almost every commodity chemical or material. Aromatic hydrocarbons are amongst the most important raw materials in the chemical industry and are obtained exclusively from fossil resources (K. Weissermel, H.-J. Arpe, in Industrial Organic Chemistry. (Wiley-VCH, 2003) pp. 313-336). There is a need to examine this dependence and make an effort to design, develop and implement new chemical processes, using renewable feedstocks rather than depleting, to meet current environmental and economic needs and to ensure the progress of future generations.

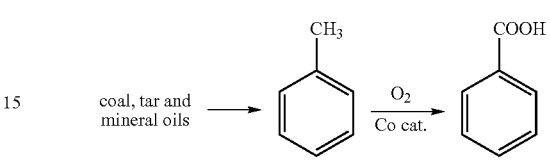

Currently, benzoic acid is prepared industrially by liquid-phase oxidation of toluene in the presence of cobalt catalysts (Dow, Snia Viscosa) (K. Weissermel, H.-J. Arpe, in Industrial Organic Chemistry. (Wiley-VCH, 2003) pp. 337-385). Oxidative decarboxylation of benzoic acid is another method used in the production of phenol (W. Buijs, Journal of Molecular Catalysis A: Chemical 146, 237 (1999/10/20, 1999)). Benzoic acid is used in the production of phenolic resins and bisphenol A for the manufacture of a wide variety of polymers and polymer additives. Benzoic acid is also used as an intermediate in the manufacture of caprolactam, terephthalic acid, dyes and perfumes, and as a preservative in food, drugs and personal care products.

Production of industrial aromatic chemicals from biomass resources could provide a sustainable alternative to traditional petroleum based manufacture and also eliminate the use of benzene-based substances hazardous to human health and the environment.

In one embodiment of the invention, the method is used to synthesize benzoic acid via formic acid-mediated deoxygenation of the glucose derivatives quinic acid and/or shikimic acid. This method eliminates the need for petroleum based starting materials.

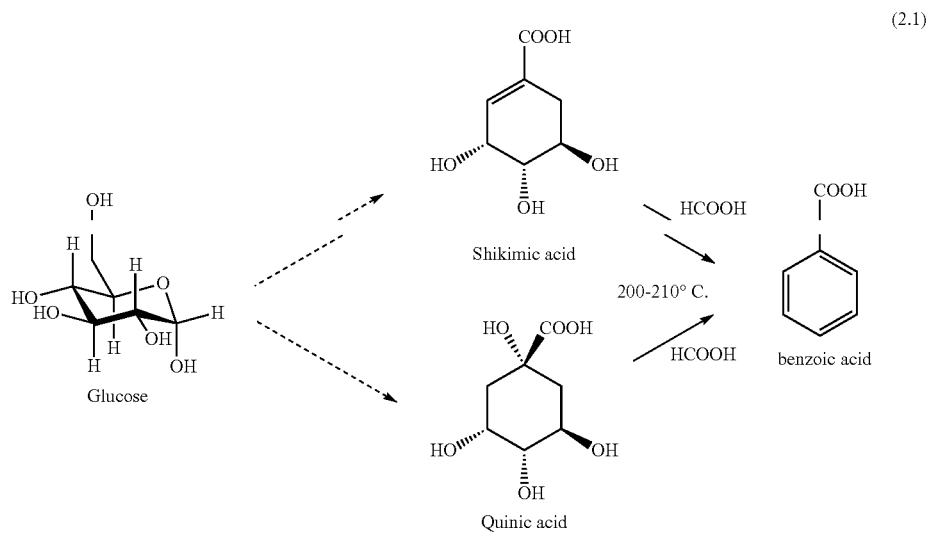

(2.1)

Quinic acid ((1R,3R,4R,5R)-1,3,4,5-tetra-hydroxycyclohexane-1-carboxylic acid) occurs widely in both plants and microorganisms, free or in the form of various esters with dihydroxycinnamic and gallic acid, known as chlorogenic acids. It can be found in such natural sources as cinchona bark, coffee beans or tobacco leaves. A cost effective environmentally clean method has been taught for the sustainable biosynthesis of quinic acid from glucose (J. W. Frost, K. M. Draths, T. L. Ward. U.S. Pat. No. 5,798,236; hereby incorporated by reference). Benzene-free synthesis of phenol and hydroquinone from quinic acid have also been reported (J. M. Gibson et al., Angew. Chem.-Int. Edit. 40, 1945 (2001); N. Q. Ran, D. R. Knop, K. M. Draths, J. W. Frost, J. Am. Chem. Soc. 123, 10927 (Nov. 7, 2001); both hereby incorporated by reference).

The reaction of quinic acid (20 mmol) and formic acid was performed in a 50 ml three neck flask fitted with a U-shaped tube that runs from a side arm of the distilling flask to a two neck collecting flask, which is connected to a cold trap and the later connected to a bubbler containing a NaOH solution. The temperature in the reaction mixture is indicated by an immersed thermometer. Nitrogen is bubbled through the mixture using a perforated tube immersed in the solution. The mixture is heated progressively while the side U-shaped tube is cooled externally using an ice-water jacket for 15 min (when the reaction mixture reaches about 170° C.). After that, the mixture is heated to about 200-210° C. and the side tube heated externally to around 130° C. to facilitate distillation of the product, benzoic acid, which is collected as white, crystalline flakes. Heating is continued until no further product deposits in the collector.

The nitrogen bubbling is maintained during the entire process. This procedure is repeated by making two more additions of formic acid (0.4 equiv). The collecting flask contained solid benzoic acid with some formic acid and water.

By continuously removing the water by distillation, the reaction can proceed nearly to completion, resulting in a yield of over 75% after collecting the pure solid compound from the collecting flask. Further purification can be made by washing the product with cold water or by resublimation.

In this procedure a solvent may be used. Such solvent should fulfill certain characteristics to be optimal for the reaction: it should have a high boiling point, it should be thermally and chemically stable and it should be polar enough to solve polyhydroxylated compounds. Sulfolane (tetramethylene sulfone) is found to be an excellent solvent for the reaction. Sulfolane is a highly polar, very stable and a water soluble compound that is used industrially for the purification of aromatic hydrocarbons and in several extractive distillations.

The reaction is performed using the following set-up and procedure: quinic acid (20 mmol) was first dissolved in sulfolane at room temperature in a 50 ml three neck flask fitted with a fractioning column connected to a collecting flask through a U-shaped tube. The temperature in the reaction mixture is indicated by an immersed thermometer and nitrogen is bubbled through the mixture using a perforated tube immersed in the solution. Formic acid is then added and the mixture is heated over a preheated oil bath to 200-220° C. for a sufficient period of time. After that, the procedure is repeated adding another aliquot of formic acid. The reaction can be monitored by $^1$H NMR taking aliquots from the reaction mixture. Eventually the conversion of quinic acid is complete. Benzoic acid is isolated from the reaction mixture by extraction with ethyl ether and isolated removing the solvent at reduced pressure to give the product in a yield of over 75%.

(2.2)

The above chemical structures, reagents, reactions and examples are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of preparing an olefin comprising: (a) providing a composition comprising the polyol, (b) heating the composition in the absence of oxygen, and (c) introducing the carboxylic acid to the composition wherein the introducing step occurs prior to, at the same time as, or subsequent to the heating step; wherein the composition is exposed to an inert atmosphere at any time during the heating step.

2. The method of claim 1, wherein the composition further comprises a solvent.

3. The method of claim 2, wherein the solvent is tetraglyme, sulfolane, or water.

4. The method of claim 1, wherein the composition is exposed to an inert atmosphere at any time during the heating step.

5. The method of claim 1, wherein the polyol is a diol, triol, monoanhydro sugar polyol, sugar, or a formic acid ester thereof.

6. The method of claim 1, the carboxylic acid is formic acid.

7. The method of claim 1, wherein the polyol is obtained from a biomass source.

8. The method of claim 5, wherein polyol is 1,2-hexanediol, 1,2-octanediol, 1,2-decanediol, 1,2-dodecanediol, 1,2-tetradecanediol, 1,2-cyclooctanediol, 1,2-cyclohexanediol, 1,2-cyclopentanediol, glycerol, 1,4-anhydroerythritol, 1,2,6-trihydroxyhexane, 1,2,3-butanetriol, 1,2,3-hexanetriol, 1,2,3-cyclohexanetriol, xylitol, sorbitol, arabinitol, ribitol, mannitol, galactitol, iditol, erythritol, threitol, isomalt, lactitol, glucose, fructose, sucrose, lactose, maltose, shikimic acid, quinic acid, or a mixture thereof.

9. The method of claim 1, wherein the heating step comprises heating the composition to a temperature from 100° C. to 300° C.

10. The method of claim 9, wherein the heating step comprises heating the composition to a temperature from 200° C. to 300° C.

11. The method of claim 10, wherein the heating step comprises heating the composition to a temperature from 220° C. to 250° C.

12. The method of claim 1, wherein the yield of the olefin is at least 50%.

13. The method of claim 1, wherein the heating step comprises heating the composition until it is molten.

14. The method of claim 1, further comprising separating the olefin from the rest of the composition.

15. The method of claim 1, further comprising neutralizing the olefin.

16. The method of claim 1, further comprising distilling the olefin.

17. The method of claim 1, wherein the olefin is allyl alcohol, and the polyol is glycerol.

18. The method of claim 1, wherein the olefin is 2,5-dihydrofuran or 1,3-butadiene, and the polyol is erythritol.

19. The method of claim 1, wherein the olefin is 1-octene, and the polyol is 1,2-octanediol.

20. The method of claim 1, wherein the olefin is benzoic acid, and the polyol is shikimic acid or quinic acid.

21. A method of synthesis of allyl alcohol from glycerol, comprising the steps of: providing glycerol and a carboxylic acid to a reaction mixture, heating the reaction mixture under an inert atmosphere in the absence of oxygen, and distilling allyl alcohol from the reaction mixture, whereby allyl alcohol is produced at a yield of about 80% or greater.

22. The method of claim 21, wherein the carboxylic acid is formic acid.

23. The method of claim 21, wherein the inert atmosphere is an inert gas.

24. The method of claim 23, wherein the inert gas is argon or nitrogen.

25. A process for synthesis of allyl alcohol from glycerol, comprising the steps of: (a) providing glycerol and formic acid to a reaction mixture, (b) heating the reaction mixture under an inert atmosphere in the absence of oxygen to between about 230° C. to about 240° C., and (c) distilling allyl alcohol from the reaction mixture, whereby allyl alcohol is produced at a yield of about 80% or greater.

26. The process of claim 25, wherein the inert atmosphere is an inert gas.

27. The process of claim 26, wherein the inert gas is argon or nitrogen.

28. The process of claim 25, wherein in the heating step (b), the reaction mixture is heated to about 235° C.

29. The process of claim 25, wherein during the distillation step (c), the reaction mixture is heated to between about 230° C. and about 240° C.

30. The method of claim 12, wherein the yield of the olefin is at least 80%.

31. The method of claim 30, wherein the yield of the olefin is at least 90%.

32. The method of claim 31, wherein the yield of the olefin is at least essentially 100%.

\* \* \* \* \*